United States Patent
Shi

(10) Patent No.: US 10,925,531 B2
(45) Date of Patent: Feb. 23, 2021

(54) INFANT PERIPHERAL LANCING DEVICE HAVING SAFETY BUCKLE TURN LOCK AND ANTI-BACKWARD PUSH BUTTON

(71) Applicant: SUZHOU SCIENCE & TECHNOLOGY TOWER STERILANCE MEDICAL INSTRUMENT CO., LTD, Jiangsu (CN)

(72) Inventor: Guoping Shi, Suzhou (CN)

(73) Assignee: SUZHOU SCIENCE & TECHNOLOGY TOWER STERILANCE MEDICAL INSTRUMENT CO., LTD, Suzhou (CN)

( * ) Notice: Subject to any disclaimer, the term of this patent is extended or adjusted under 35 U.S.C. 154(b) by 553 days.

(21) Appl. No.: 15/301,771

(22) PCT Filed: Mar. 31, 2015

(86) PCT No.: PCT/CN2015/075555
§ 371 (c)(1),
(2) Date: Oct. 4, 2016

(87) PCT Pub. No.: WO2015/149691
PCT Pub. Date: Oct. 8, 2015

(65) Prior Publication Data
US 2017/0042459 A1    Feb. 16, 2017

(30) Foreign Application Priority Data
Apr. 4, 2014 (CN) .......................... 201410135399.4

(51) Int. Cl.
*A61B 5/15* (2006.01)
*A61B 5/151* (2006.01)

(52) U.S. Cl.
CPC ........ *A61B 5/150687* (2013.01); *A61B 5/151* (2013.01); *A61B 5/150022* (2013.01);
(Continued)

(58) Field of Classification Search
CPC ........ A61B 5/150687; A61B 5/150022; A61B 5/15113; A61B 5/15126; A61B 5/15128; A61B 5/150259; A61B 5/150885
See application file for complete search history.

(56) References Cited

U.S. PATENT DOCUMENTS 4,628,929 A    12/1986 Intengan et al.
5,314,441 A    5/1994 Cusack et al.
(Continued)

FOREIGN PATENT DOCUMENTS

CN    1541080 A    10/2004
CN    101317760 A    12/2008
CN    103932715 A    7/2014
(Continued)

OTHER PUBLICATIONS

Jun. 16, 2015 International Search Report issued in International Patent Application No. PCT/CN2015/075555.
Oct. 4, 2016 International Preliminary Report on Patentability issued in International Patent Application No. PCT/CN2015/075555.

*Primary Examiner* — Devin B Henson
(74) *Attorney, Agent, or Firm* — Oliff PLC

(57) ABSTRACT

An infant peripheral lancing device having safety buckle turn lock and anti-backward push button, wherein the safety mechanism is a safety buckle rotationally connected on a housing, and the first occupation gesture of the safety buckle during movement is between a push button and the housing and locks the push button; the second occupation gesture is in unlocking position. The push button is set with a locking mechanism, which comprises a first locking part on the push button and a second locking part on the housing or the cam and when the push button is moved backward, the first
(Continued)

locking part and the second locking part meet to form a locking state. This solution always connects the safety buckle and the housing to prevent an accidental disconnection or loss and the lancing device present invention locks the push button automatically after using to make it easy for the user to identify the state of the push button.

17 Claims, 9 Drawing Sheets

(52) U.S. Cl.
CPC ...... *A61B 5/15113* (2013.01); *A61B 5/15117* (2013.01); *A61B 5/15128* (2013.01); *A61B 5/15144* (2013.01); *A61B 5/150442* (2013.01); *A61B 5/150916* (2013.01); *A61B 5/150259* (2013.01); *A61B 2503/04* (2013.01)

(56) References Cited

U.S. PATENT DOCUMENTS

| | | | |
|---|---|---|---|
| 5,797,940 A * | 8/1998 | Mawhirt | A61B 17/32093 |
| | | | 606/167 |
| 6,958,072 B2 | 10/2005 | Schraga | |
| 7,575,583 B1 | 8/2009 | Schraga | |
| 7,998,161 B2 | 8/2011 | Shi | |
| 8,715,307 B2 * | 5/2014 | Sun | A61B 5/150022 |
| | | | 606/182 |
| 9,724,031 B2 * | 8/2017 | Yi | A61B 5/15128 |
| 2003/0050656 A1 | 3/2003 | Schraga | |
| 2010/0010529 A1 | 1/2010 | Shi | |
| 2016/0331292 A1 * | 11/2016 | Leskowich | A61B 5/150503 |

FOREIGN PATENT DOCUMENTS

| | | |
|---|---|---|
| CN | 203828940 U | 9/2014 |
| WO | 03/049624 A1 | 6/2003 |

* cited by examiner

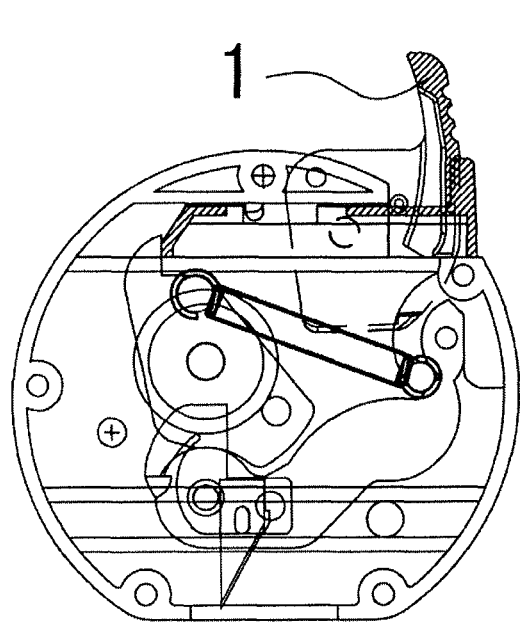
FIG. 27
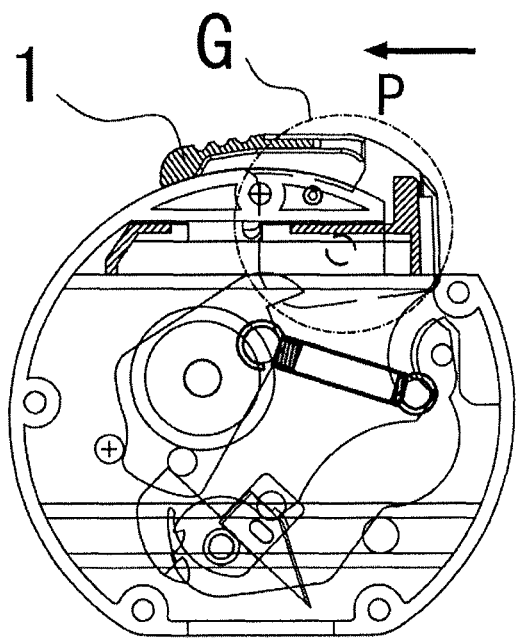
FIG. 28
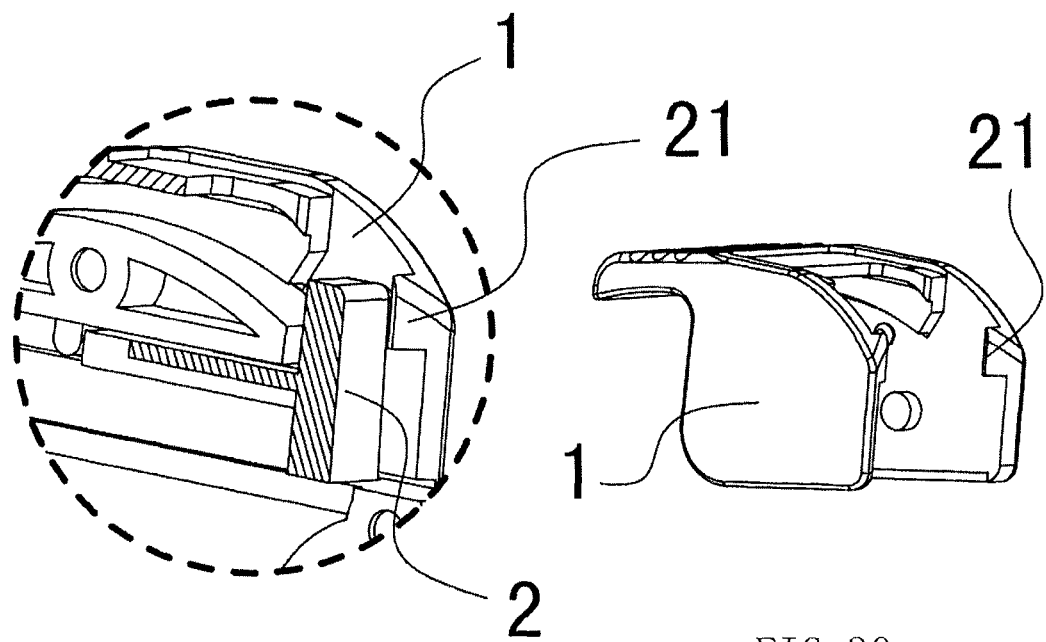
FIG. 29
FIG. 30

INFANT PERIPHERAL LANCING DEVICE HAVING SAFETY BUCKLE TURN LOCK AND ANTI-BACKWARD PUSH BUTTON

TECHNICAL FIELD

The present invention relates to the medical lancing device, especially a kind of infant peripheral lancing device having safety buckle rotation and locking function and anti-backward function after using the push button. The lancing device applies the cutting method and it's mainly used for blood sampling from the infant's heel and also used for blood sampling from other body parts.

BACKGROUND OF INVENTION

The lancing device is widely used in different medical institutions as the medical lancing device. The lancing device is divided into pricking and cutting types. The pricking type lancing device applies the pricking method on the sampling position and it's mainly used for finger sampling for the adult. The cutting type lancing device applies the cutting method on the sampling position. As the pain sense caused by cutting type is lighter than that caused by pricking sense and the sampling amount is sufficient, it's especially suitable for the infant, especially suitable for the blood sampling from the heel of infant.

Chinese patent CN101317760A disclosed the invention patent application with the title of disposable safety cutting type lancing device. The application presents a kind of solution of typical cutting type lancing device. The applicant knows that the lancing device has been widely used with good effect, but it still has some shortcoming during the practical application, for example, in order to prevent the unintentional triggering of blood collection mechanism, the protection cover is set between the push button and housing as the safety mechanism. When the lancing device is used, remove the protection cover first and then use the finger to push the push button for blood sampling. After the protection cover is removed from the lancing device to become a separate component and it's very small to get lost easily. Therefore, it's not convenient to control the waste and if the protection cover is left on the working table and eaten by the children, it will cause the accident. On the other hand, the medical staff said that the protection cover is too small to be flown away during the disassembly, which could cause the inconvenient use and improper treatment of medical waste. For example, after the pushing the push button, there is no locking mechanism in the cover, so the push button is loose in relation to the cover, which could cause the noise and make it difficult for the user to identify the use status of lancing device according to the position of push button.

Therefore, the aim of the present invention is to design a kind of new safety mechanism and push button locking and anti-backward mechanism.

DISCLOSURE OF THE INVENTION

The aim of present invention is to design a kind of new rotation impact safety mechanism and push button locking and anti-backward mechanism to match the cutting type lancing device and solve the problem of separate design of safety mechanism and looseness of push button after triggering mentioned in the above background.

In order to achieve the above purpose, the present invention applies the technical solution: An infant peripheral lancing device having safety buckle turn lock and anti-backward push button, comprising a housing (3) and a trigger, which is a push type mechanism comprising a push button slideably located on the housing, and a safety mechanism is set between the push button and the housing to prevent the unintentional triggering of blood collection mechanism, wherein;

the safety mechanism is a safety buckle, which is a clamp turnably connected to the housing and has two occupation gestures in the rotation route in relation to the housing: the first occupation gesture is clamped between the push button and the housing to force the push button to be in the locking state before triggering; the second occupation gesture is in the position disengaging from the first occupation state to make the push button be in the unlocking state;

between the push button and the housing, or between the push button and the cam in the blood collection mechanism, or between the push button and the safety buckle, a locking mechanism is set to lock the push button after triggering, and the locking mechanism consists of a first locking part on the push button and a second locking part set on the housing or the cam or the safety buckle, the first locking part and the second locking part meet during the sliding of the push button and when the push button slides in the triggering direction, the first locking part and the second locking part meet to form a sliding matching, but when the push button slides in the returning direction, the first locking part and the second locking part meet to form a locking matching.

The above described technical solution is explained as follows:

1. In above described technical solution, the "housing" means the case structure of lancing device. The "blood collection mechanism" means the cutting type blood collection mechanism. The "safety mechanism" means the mechanism between the push button and housing to prevent the unintentional triggering of blood collection mechanism.

2. In above described technical solution, the following method is applied to realize the rotational connection of safety buckle: at the rotational connection of safety buckle and housing, one of the safety buckle and housing is set with the rotation shaft and the other is set with the rotation shaft hole, so that the rotation shaft and rotation shaft hole work together to realize the rotational connection of the safety buckle in relation to the housing.

3. In above described technical solution, the following method is applied to realize the rotational locating of safety buckle: in the rotational route of safety buckle in relation to the housing, the locating mechanism is set between the safety buckle and housing and it comprises the concave point in one of them and the convex point in the other. The locating mechanism makes the safety buckle have two locating positions in the rotational route in relation to the housing: one position corresponding to the first occupation gesture and the other position corresponding to the second occupation gesture.

4. In above described technical solution, the locking mechanism to lock the triggered push button comprises the following four structures:

(1) the first locking part is the slot set on the push button and the second locking part is the wedge protruding rib on the housing, so the slot on the push button and the wedge protruding rib on the housing form the locking mechanism;

(2) the first locking part is the flexible hook set on the push button and the second locking part is the convex on the housing, so the flexible hook on the push button and the convex on the housing form the locking mechanism;

(3) the first locking part is the limit stop set on the push button and the second locking part is the locking arm on the cam, so the limit stop on the push button and the locking arm on the cam form the locking mechanism;

(4) the first locking part is the flexible arm set on the push button and the second locking part is the stopper on the housing, so the flexible arm on the push button and the stopper on the housing form the locking mechanism;

(5) the first locking part is the rear end face set on the push button and the second locking part is the barb on the safety buckle;

(6) the first locking part consists of the convex after the rotation shaft on the safety buckle passing through the rotation shaft hole on the housing and the second locking part consists of the flange formed by the connection of inclined surface and straight surface on the push button.

The principle and effect of present invention are described as follows:

Firstly, in order to solve the problems caused by the separate component design of safety mechanism of cutting type lancing device, the present invention designs the safety mechanism (safety buckle) into the structure of housing rotational connection and the locking state or unlocking state of push button through the different occupation gestures of safety buckle in relation to the housing, and the safety buckle is always connected with the housing before and after functioning of safety buckle to avoid the accidental disconnection or loss, so it solves the problems of the prior art to make the medical waste control and treatment safer and more convenient.

Secondly, in order to solve the problems of looseness of push button, noise and difficulty to identify the use status of push button after the triggering, the present invention especially designs the locking mechanism to prevent the return of push button between the push button and the housing or cam and during the operation of lancing device, use the finger to push the push button to trigger the blood collection mechanism and the locking mechanism automatically locks the push button in position after the triggering, so the push button doesn't make noise and the user could easily identify the use status of push button, which avoids the unnecessary troubles.

BRIEF DESCRIPTION OF THE DRAWINGS

FIG. 27 is the status of lancing device before triggering in the embodiment 5 of present invention;

FIG. 28 is the status of lancing device after triggering in the embodiment 5 of present invention;

FIG. 29 is a local enlarged view of G in FIG. 28;

FIG. 30 is the perspective view of rotational locking type safety buckle in FIG. 27 or 28;

In the above figures: 1. safety buckle, 2, push button; 3. housing; 4. cam; 5. spring; 6. principal arm; 7. secondary arm; 8. blade; 9. rotation shaft; 10. limit convex; 11, rotation shaft hole; 12. limit hole; 13. wedge protruding rib; 14. slot; 15. convex; 16. flexible hook; 17. limit stop; 18. locking arm; 19. stopper; 20. flexible arm; 21. barb; 22. primary placement slot; 23. secondary placement slot; 24. inclined surface; 25. straight surface.

SPECIFIC EMBODIMENT

With reference to the accompanying drawings and embodiment, the present invention will be described in detail.

Embodiment 1

Figure 3:
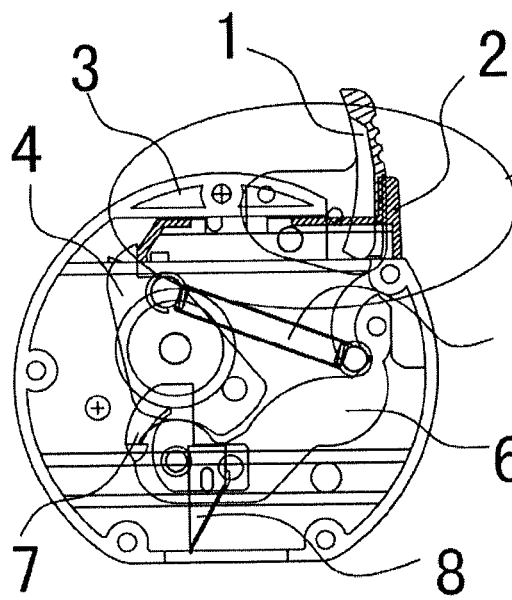
FIG. 3 is the status of lancing device before triggering in the embodiment 1 of present invention.
Figure 4:
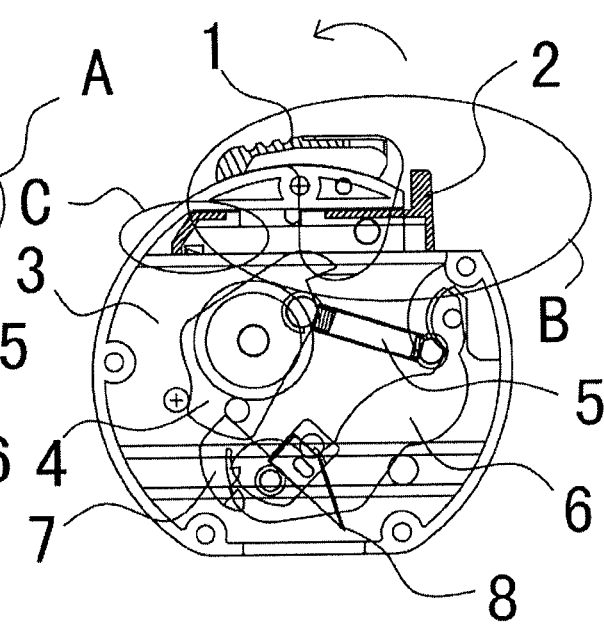
FIG. 4 is the status of lancing device after triggering in the embodiment 1 of present invention.

A kind of infant peripheral lancing device having safety buckle turn lock and anti-backward push button As shown in FIG. 1-11, the lancing device comprises housing 3, blood collection mechanism and trigger, wherein:

the blood collection mechanism comprises the cam 4, spring 5, principal arm 6, secondary arm 7 and blade 8 (refer to FIGS. 3 and 4).

Figure 1:
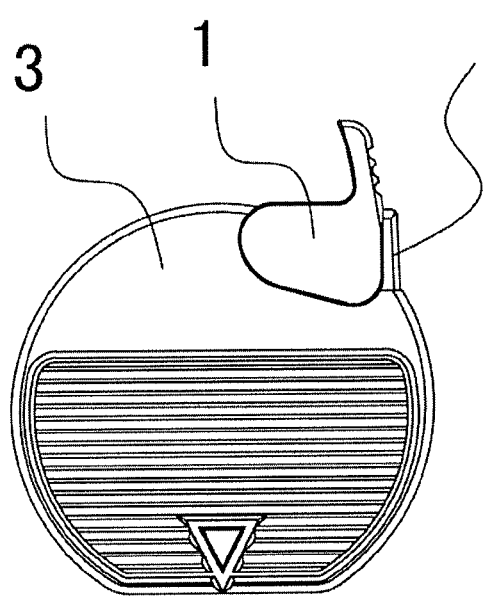
FIG. 1 is the status of lancing device's safety buckle of the present invention before releasing.
Figure 2:
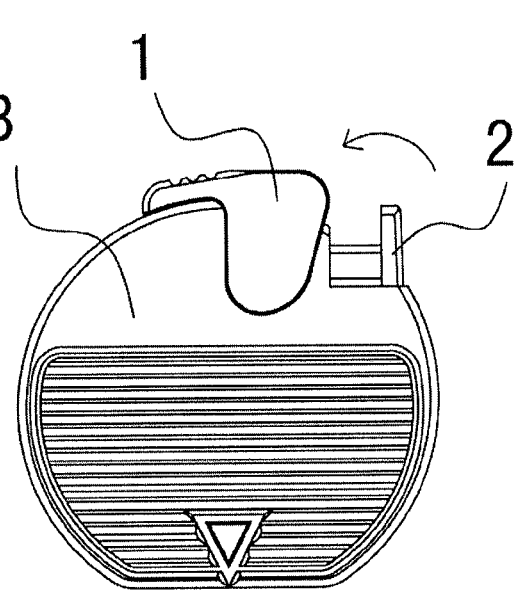
FIG. 2 is the status of lancing device's safety buckle of the present invention after releasing.
Figure 6:
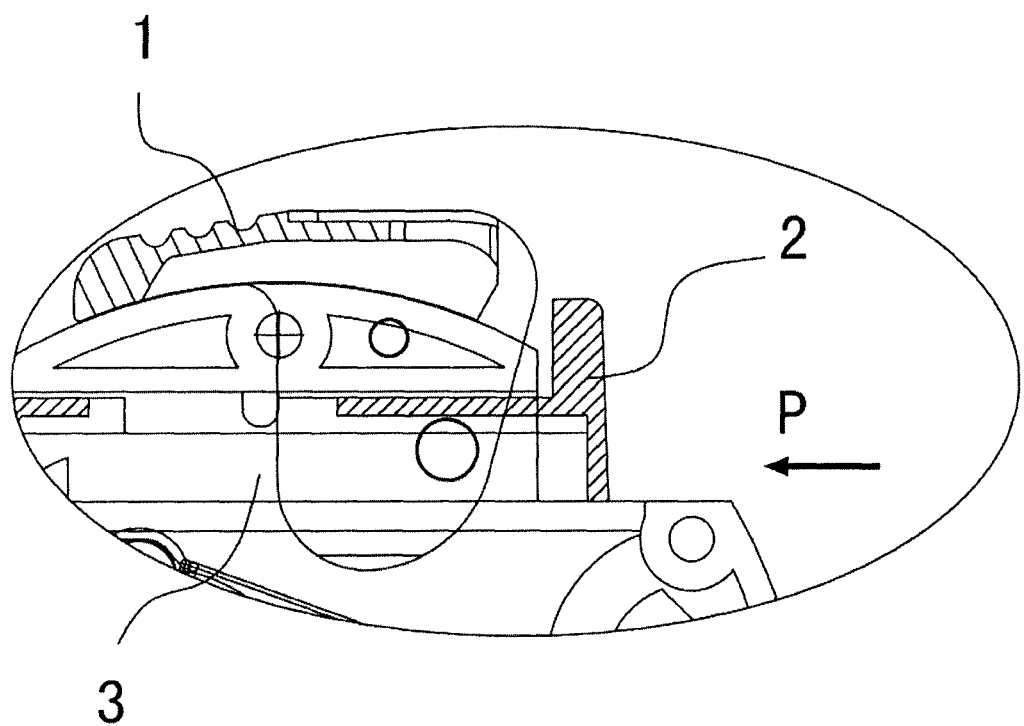
FIG. 6 is a local enlarged view of B in FIG. 4.
Figure 7:
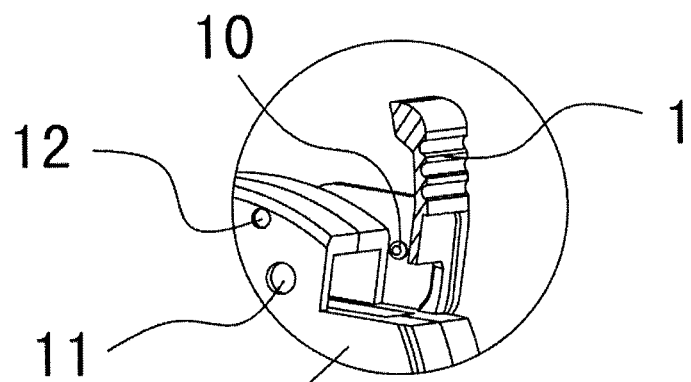
FIG. 7 is the enlarged view of connection position of housing and safety buckle in the embodiment 1 of present invention.
Figure 8:
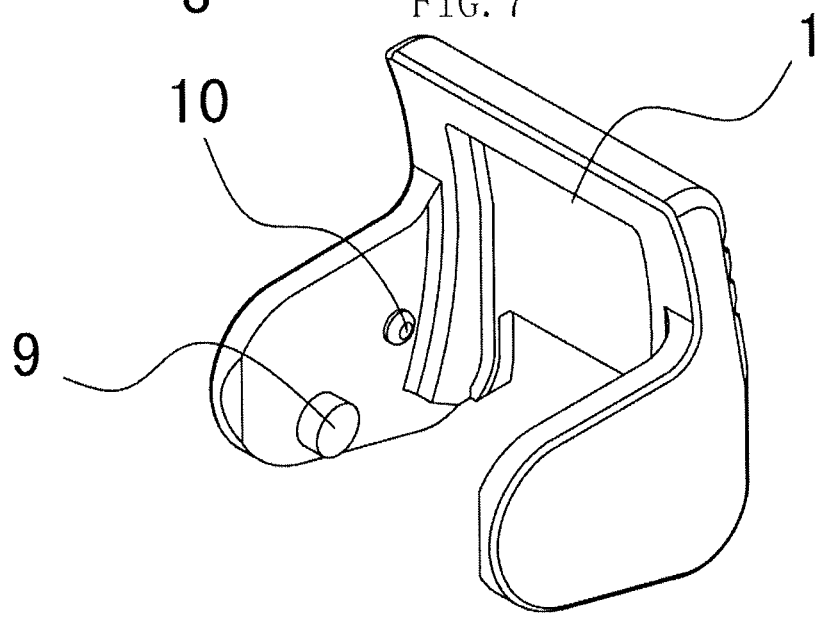
FIG. 8 is the perspective view of safety buckle in the embodiment 1 of present invention.
Figure 9:
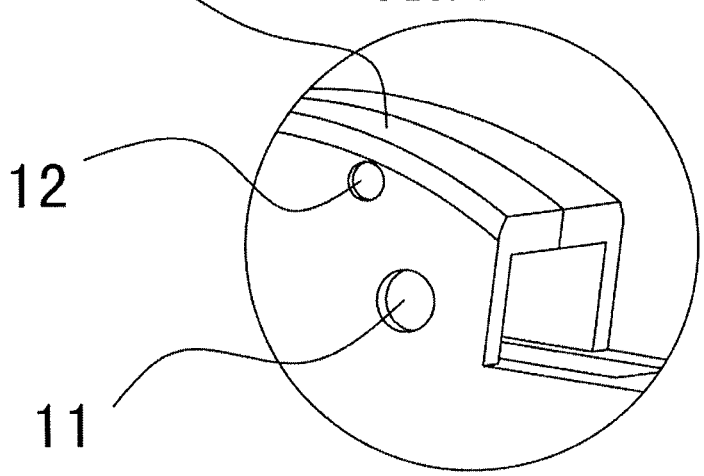
FIG. 9 is the local enlarged view of housing in the embodiment 1 of present invention.
Figures 10, 11:
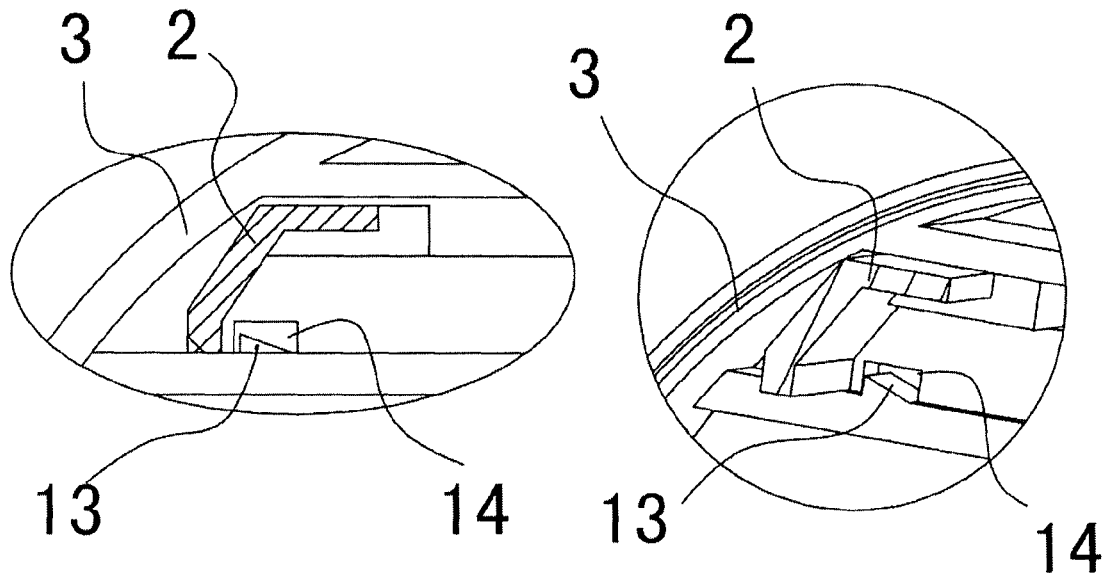
FIG. 10 is a local enlarged view of C in FIG. 4.
FIG. 11 is the perspective view of FIG. 10.
Figures 12, 13:
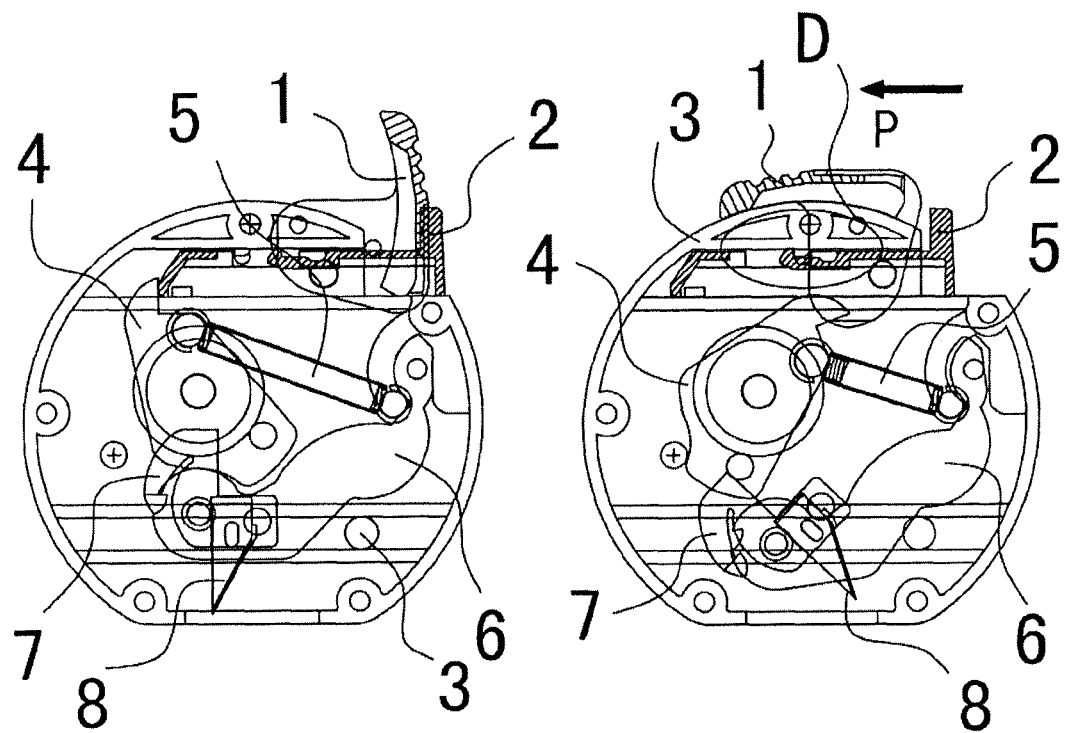
FIG. 12 is the status of lancing device before triggering in the embodiment 2 of present invention.
FIG. 13 is the status of lancing device after triggering in the embodiment 2 of present invention.
Figures 14, 15:
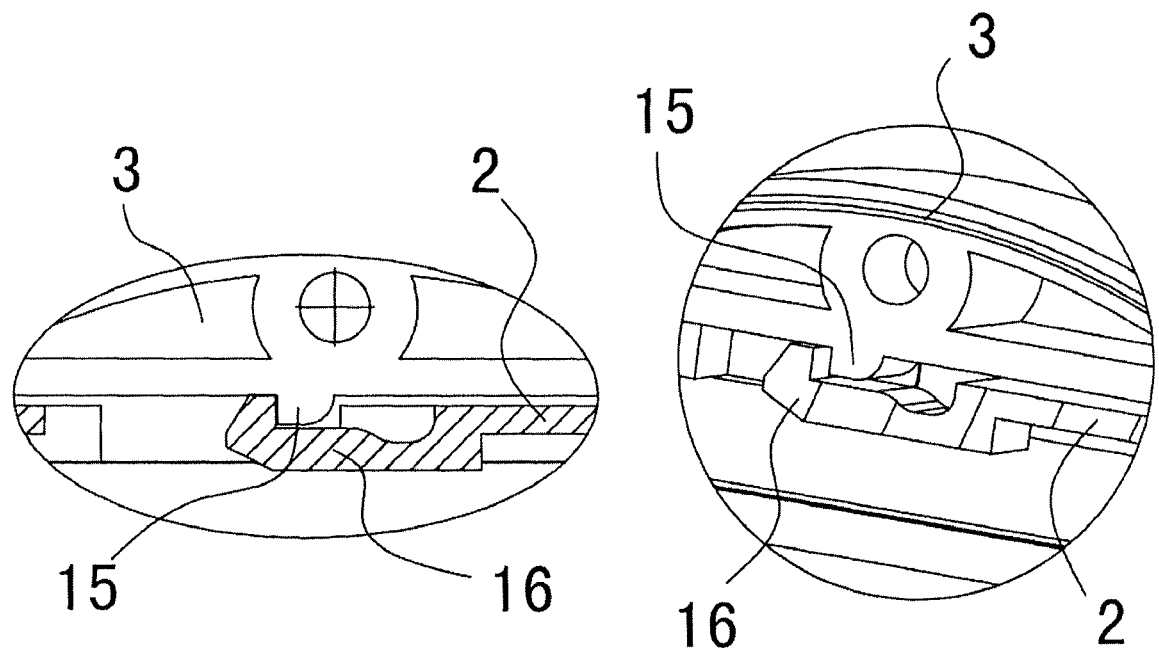
FIG. 14 is a local enlarged view of D in FIG. 13.
FIG. 15 is the perspective view of FIG. 14.
Figures 16, 17:
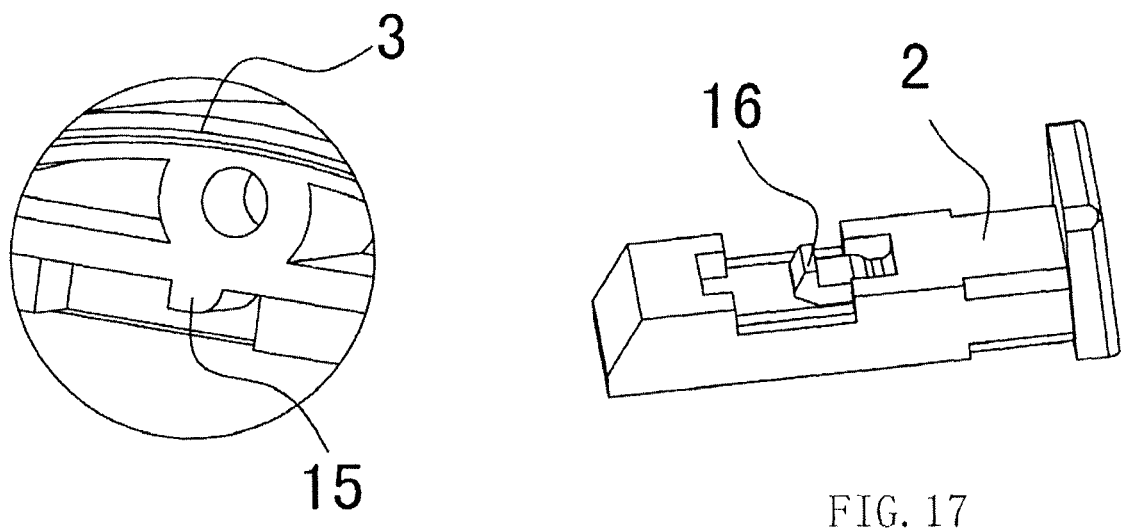
FIG. 16 is perspective view of housing's convex in the embodiment 2 of present invention.
FIG. 17 is perspective view of the flexible hook on the push button in the embodiment 2 of present invention.
Figures 18, 19:
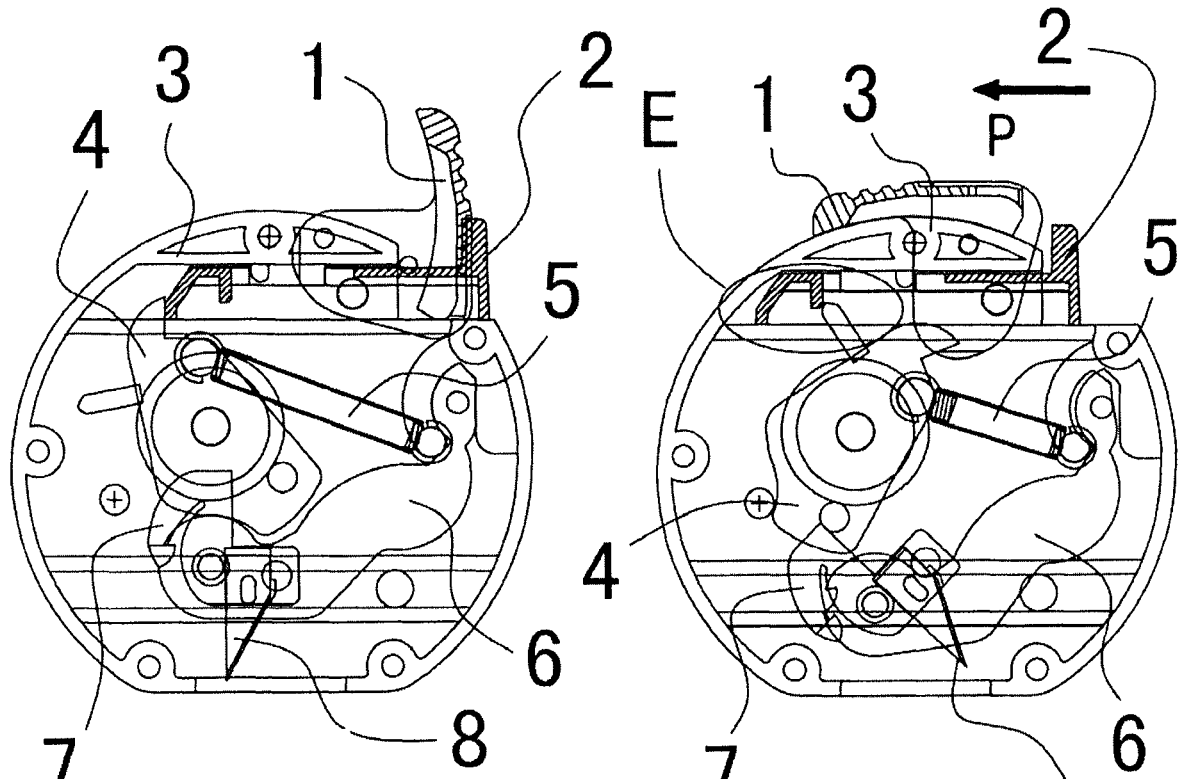
FIG. 18 is the status of lancing device before triggering in the embodiment 3 of present invention.
FIG. 19 is the status of lancing device after triggering in the embodiment 3 of present invention.
Figures 20, 21:
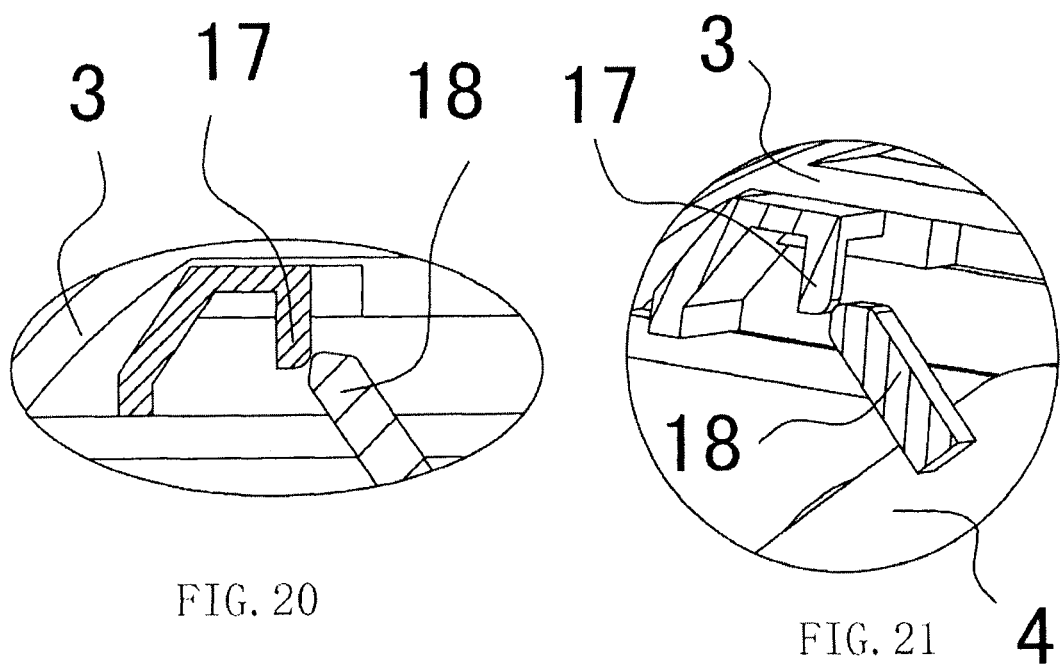
FIG. 20 is a local enlarged view of E in FIG. 19.
FIG. 21 is the perspective view of FIG. 20.
Figures 22, 23:
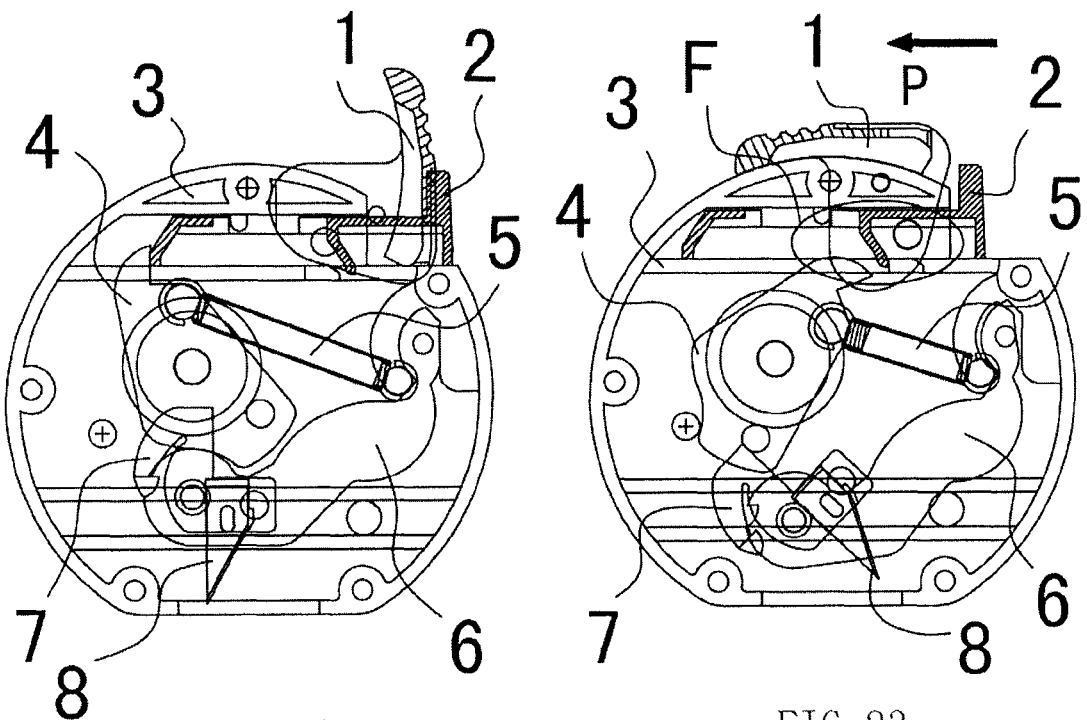
FIG. 22 is the status of lancing device before triggering in the embodiment 4 of present invention.
FIG. 23 is the status of lancing device after triggering in the embodiment 4 of present invention.
Figures 24, 25:
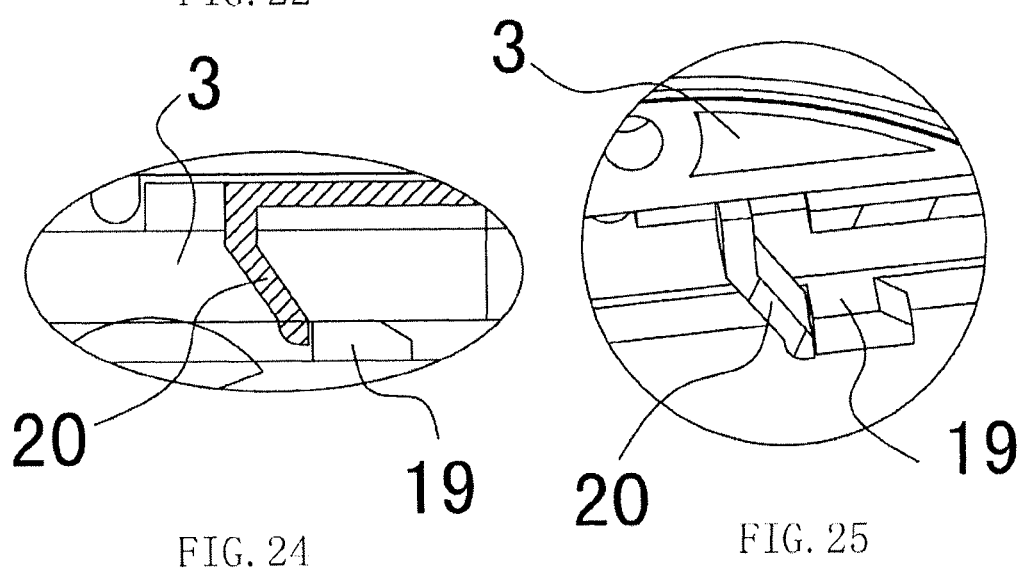
FIG. 24 is a local enlarged view of F in FIG. 23.
FIG. 25 is the perspective view of FIG. 24.
Figure 26:
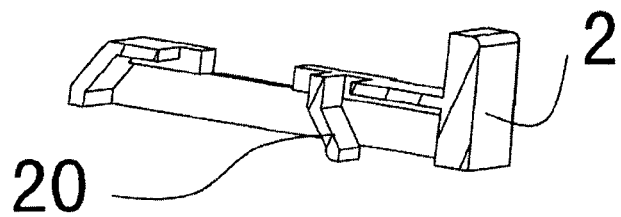
FIG. 26 is perspective view of the push button in the embodiment 4 of present invention.
Figure 31:
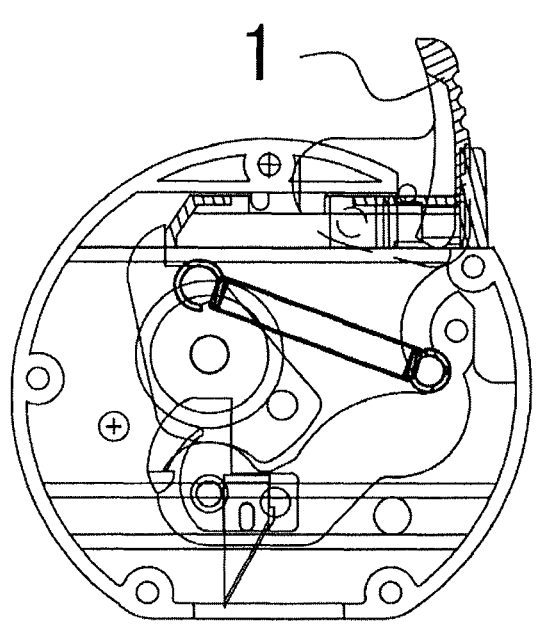
FIG. 31 is the status of lancing device before triggering in the embodiment 6 of present invention.
Figure 32:
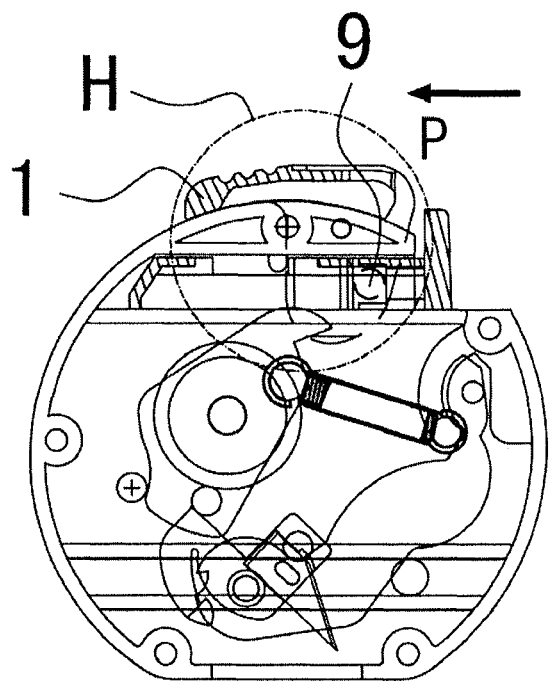
FIG. 32 is the status of lancing device after triggering in the embodiment 6 of present invention.
Figure 33:
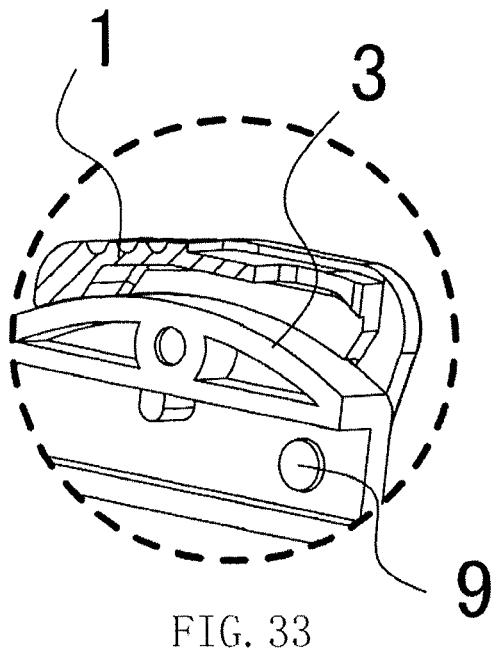
FIG. 33 is a local enlarged view of H in FIG. 32.

The trigger is a push type mechanism comprising a push button 2 slideably located on the housing 3 and the safety mechanism is set between the push button 2 and housing 3 to prevent the unintentional triggering of blood collection mechanism, wherein:

the safety mechanism is a safety buckle 1, which is the clamp turnably connected on the housing 3 and has two occupation gestures in the rotation route in relation to the housing 3: the first occupation gesture is clamped between the push button 2 and housing 3 to force the push button to be in the locking state before triggering (refer to FIGS. 1, 3 and 5); the second occupation gesture is in the position disengaging from the first occupation state to make the push button 2 be in the unlocking state (refer to FIGS. 2, 4 and 6);

In order to realize the reliable rotational connection of safety buckle 1 and housing 3, it's possible to design the hole/shaft connection mechanism at the connection of safety buckle 1 and housing 3, i.e. one of safety buckle 1 and housing 3 is set with the rotation shaft 9, and the other is set with the rotation shaft hole 11, so that rotation shaft 9 and rotation shaft hole 11 work together to realize the rotational connection of safety buckle 1 in relation to the housing 3. In this embodiment, as shown in FIGS. 7, 8 and 9, the rotation shaft 9 is set on the safety buckle 1 (refer to FIG. 8), the rotation shaft hole 11 is set on the housing 3 (refer to FIG. 9) and the rotation shaft 9 and rotation shaft hole 11 work together (refer to FIG. 7). Of course, the positions of rotation shaft 9 and rotation shaft hole 11 could be switched, i.e. the rotation shaft 9 is set in the housing 3 and the rotation shaft hole 11 is set in the safety buckle 1. It could be thought of by the technicians in this field.

3. In order to realize the rotational locating of safety buckle 1 in relation to the housing 3, in the rotational route of safety buckle 1 in relation to the housing 3, the locating mechanism is set between the safety buckle 1 and housing 3 and it comprises the concave point in one of them and the convex point in the other. The locating mechanism makes the safety buckle 1 have two locating positions in the rotational route in relation to the housing 3: one position corresponding to the first occupation gesture and the other position corresponding to the second occupation gesture. In this embodiment, as shown in FIGS. 7, 8 and 9, the safety buckle 1 is set with the limit convex 10 (refer to FIG. 8) and the housing is set with the limit hole 12 (refer to FIG. 9). Of course, the positions could be switched and it could be thought of by the technicians in this field.

In order to solve the problems of looseness of push button 2, noise and difficulty to identify the use status of push button after the triggering, this solution sets a locking mechanism between the push button 2 and housing 3 to lock the push button 2 after the triggering.

the locking mechanism comprises the slot 14 set on the push button 2 and the wedge protruding rib 13 set on the housing 3 (refer to FIGS. 10 and 11), and the slot 14 is the first locking part and the wedge protruding rib 13 is the second locking part, so the slot 14 on the push button 2 and the wedge protruding rib 13 on the housing 3 work together to form the locking mechanism.

Figure 5:
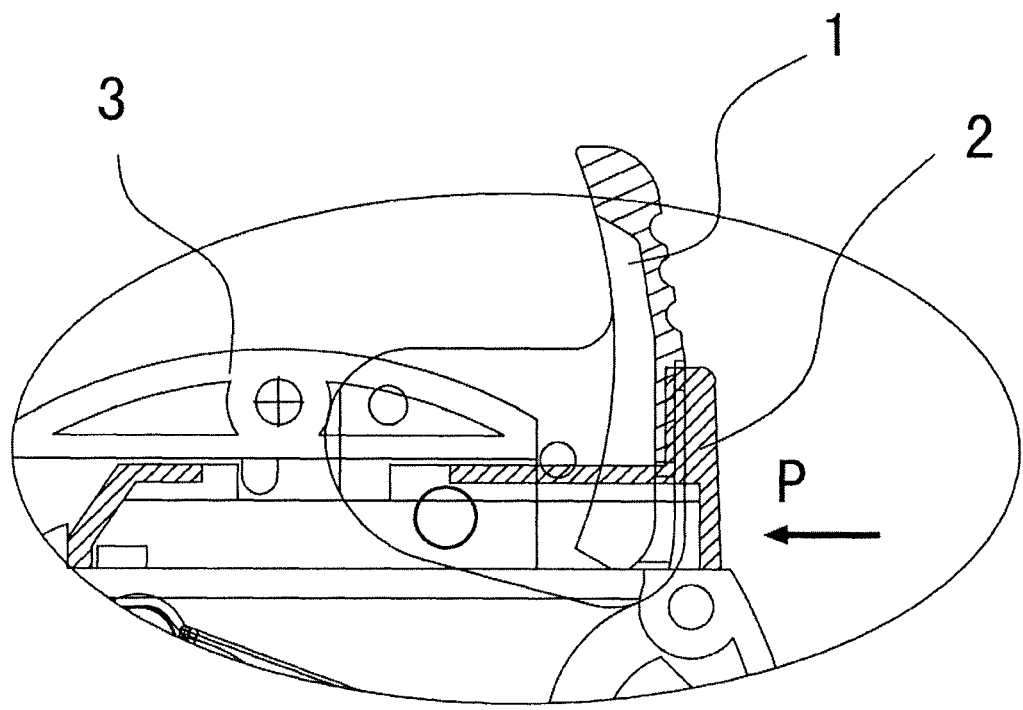
FIG. 5 is a local enlarged view of A in FIG. 3.

The operation process of this embodiment is described as follows:

1. When the user doesn't release the safety buckle 1 as shown in FIGS. 1, 3 and 5, the safety buckle 1 is clamped and fixed by the binding force between the housing 3 and push button 2, so that the push button 2 is in the locking state before firing with the purpose to avoid the harm caused by the misoperation. Under such state, the limit convex 10 on the safety buckle 1 (refer to FIG. 8) is blocked by the side wall of housing 3 (refer to FIG. 7), so that the push button 2 is in the locking state (refer to FIG. 5) and could not move in the P direction, so that the lancing device is in the state of ready to be fired.

2. When the user uses the lancing device, firstly turn and release the safety buckle 1 as shown in FIGS. 1, 4 and 6 to turn the push button 2 to the final position to be locked with the housing 3, i.e. the limit convex 10 on the safety buckle 1 (FIG. 8) is in the limit hole 12 on the housing 3 (FIG. 9) to be locked, so the push button 2 is ready to be fired and then push the push button 2 in P direction to trigger the blood collection mechanism for blood collection. After the blood collection, the safety buckle 1 and housing 3 are locked together, which solves the problem of difficulty to control the separate safety buckle after the use. And this mechanism also makes it easy and convenient to use the lancing device with one hand.

3. When the user pushes the push button 2 in P direction to trigger the blood collection mechanism, the slot 14 at front end of push button 2 moves across the wedge protruding rib 1 on the housing 3 to be inserted (FIG. 10 and FIG. 11) and could not be moved, so the push button 2 is in the locking state, which solves the problem that the push button 2 could be moved backward after triggering and makes it easy for the user to identify the use state of push button 2.

Embodiment 2

A kind of infant peripheral lancing device having safety buckle turn lock and anti-backward push button As shown in FIG. 12-17, the lancing device comprises housing 3, blood collection mechanism and trigger. The difference between embodiment 2 and embodiment 1 is:

the locking mechanism comprises the flexible hook 16 set on the push button 2 and the convex 15 set on the housing 3 (FIGS. 14, 15, 16 and 17), and the flexible hook 16 is the first locking part and the convex 15 is the second locking part, so the flexible hook 16 on the push button 2 and the convex 15 on the housing 3 work together to form the locking mechanism.

3. When the user pushes the push button 2 in P direction to trigger the blood collection mechanism, the flexible hook 16 at front end of push button 2 moves across the convex 15 on the housing 3 to be inserted (FIG. 14 and FIG. 15) and could not be moved, so the push button 2 is in the locking state, which solves the problem that the push button 2 could be moved backward after triggering and makes it easy for the user to identify the use state of push button 2.

The others is the same as embodiment 1 and is not described repeatedly.

Embodiment 3

A kind of infant peripheral lancing device having safety buckle turn lock and anti-backward push button As shown in FIG. 18-21 the lancing device comprises housing 3, blood collection mechanism and trigger. The difference between embodiment 3 and embodiment 1 is:

the locking mechanism comprises the limit stop 17 set on the push button 2 and the locking arm 18 set on the cam 4 (FIGS. 20 and 21), and the limit stop 17 is the first locking part and the locking arm 18 is the second locking part, so the limit stop 17 on the push button 2 and the locking arm 18 set on the cam 4 work together to form the locking mechanism.

When the user pushes the push button 2 in P direction to trigger the blood collection mechanism, the cam 4 turns clockwise by the force of spring 5 and the locking arm 18 on the cam 4 stops after moving across the limit stop 17 at front end of push button 2 and blocks the backward route of limit stop 17 (FIG. 20 and FIG. 21), which could not be moved, so the push button 2 is in the locking state, which solves the problem that the push button 2 could be moved backward after triggering and makes it easy for the user to identify the use state of push button 2.

The others is the same as embodiment 1 and is not described repeatedly.

Embodiment 4

A kind of infant peripheral lancing device having safety buckle turn lock and anti-backward push button As shown in FIG. 22-26, the lancing device comprises housing 3, blood collection mechanism and trigger. The difference between embodiment 4 and embodiment 1 is:

the locking mechanism comprises the flexible arm 20 set on the push button 2 and the stopper 19 set on the housing 3 (FIGS. 24, 25 and 26), and the flexible arm 20 is the first locking part and the stopper 19 is the second locking part, so the flexible arm 20 on the push button 2 and the stopper 19 on the housing 3 work together to form the locking mechanism.

3. When the user pushes the push button 2 in P direction to trigger the blood collection mechanism, the flexible arm 20 at front end of push button 2 moves across the stopper 19 on the housing 3 to be inserted (FIG. 24 and FIG. 15) and could not be moved, so the push button 2 is in the locking state, which solves the problem that the push button 2 could be moved backward after triggering and makes it easy for the user to identify the use state of push button 2.

The others is the same as embodiment 1 and is not described repeatedly.

Embodiment 5

A kind of infant peripheral lancing device having safety buckle turn lock and anti-backward push button As shown in FIG. 27-30, the lancing device comprises housing 3, blood collection mechanism and trigger. The difference between embodiment 5 and embodiment 1 is:

the locking mechanism comprises the rear end face set on the push button 2 and the barb 21 set on the safety buckle 1 (FIGS. 29 and 30), and the rear end face on the push button 2 is the first locking part and the barb 21 on the safety buckle 1 is the second locking part.

When the user pushes the push button 2 in P direction to trigger the blood collection mechanism, the rear end face on the push button 2 moves across the barb 21 on the safety buckle 1 and the rear end face is hooked by the barb 21 and could not be moved backward to make the push button 2 in the locking state.

The others is the same as embodiment 1 and is not described repeatedly.

Embodiment 6

A kind of infant peripheral lancing device having safety buckle turn lock and anti-backward push button As shown in FIG. 31-34, the lancing device comprises housing 3, blood collection mechanism and trigger. The difference between embodiment 6 and embodiment 1 is:

the first locking part consists of the convex (FIG. 33) after the rotation shaft 9 on the safety buckle 1 passing through the rotation shaft hole 11 on the housing 3 and the second locking part consists of the flange (FIG. 34) formed by the connection of inclined surface 24 and straight surface 25 on the push button 2.

Figure 34:
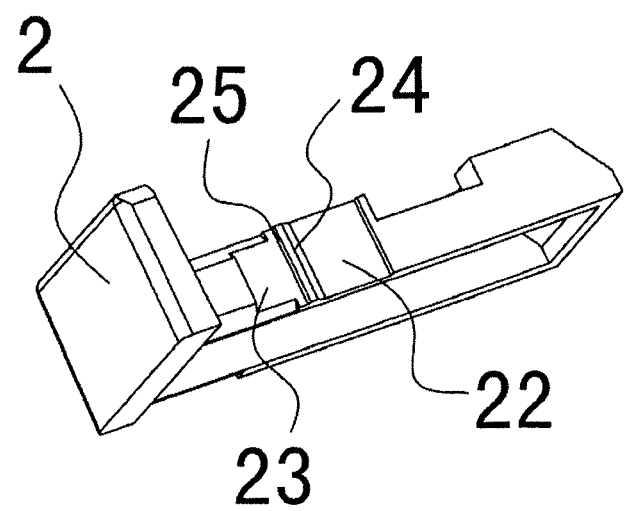
FIG. 34 is perspective view of the push button.

When the user pushes the push button 2 in P direction to trigger the blood collection mechanism, the inclined surface 24 at the side of push button 2 moves across the convex formed by the rotation shaft 9 on the safety buckle 1 and it is blocked by the straight surface 25 and could not be moved backward to make the push button 2 in the locking state. As shown in FIG. 34, the convex formed by the rotation shaft 9 before triggering is in the primary placement slot 22 and the convex formed by the rotation shaft 9 after triggering is in the secondary placement slot 23 and locked.

The others is the same as embodiment 1 and is not described repeatedly.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A lancing device having safety buckle turn lock and anti-backward push button, comprising:
    a housing,
    a trigger comprising a push button slideably located on the housing,
    a safety mechanism set between the push button and the housing to prevent unintentional triggering of a blood collection mechanism, and
    a tension spring that pulls against a rotating member, thereby causing the rotating member to rotate about a fixed axis, which in turn causes a blade of the blood collection mechanism to move toward a cutting position extended from the housing, wherein:
    the safety mechanism includes a safety buckle that is turnably connected to the housing and has two orientations in a rotation route of the safety buckle in relation to the housing, the two orientations including (i) a first orientation between the push button and the housing to force the push button to be in a locking state before triggering and (ii) a second orientation, in a position separated from the first orientation, to make the push button be in an unlocking state, the safety buckle being restricted from rotation relative to the housing in the second orientation, such that the safety buckle is held stationary relative to the housing;
    between the push button and the housing, or between the push button and the safety buckle, a locking mechanism is set to lock the push button after triggering, and the locking mechanism comprises a first locking part on the push button and a second locking part on the housing or the safety buckle, the first locking part and the second locking part meet during sliding of the push button and when the push button slides in a triggering direction, the first locking part and the second locking part meet to form a sliding engagement, but when the push button slides in a returning direction, the first locking part and the second locking part meet to form a locking engagement; and
    at a rotational connection of the safety buckle and the housing, one of the safety buckle and the housing includes a rotation shaft, and the other one includes a rotation shaft hole, so that the rotation shaft and the rotation shaft hole work together to realize the rotational connection.

2. A lancing device as claimed in claim 1, wherein: the first locking part is a slot on the push button and the second locking part is a wedge protruding rib on the housing, the wedge being in the slot after the triggering.

3. A lancing device as claimed in claim 1, wherein: the first locking part is a flexible hook on the push button and the second locking part is a convex on the housing.

4. A lancing device as claimed in claim 1, wherein: the first locking part is a flexible arm on the push button and the second locking part is a stopper on the housing.

5. A lancing device as claimed in claim 1, wherein: the second locking part includes a portion of the rotation shaft on the safety buckle that protrudes from the rotation shaft hole on the housing and the first locking part includes a flange formed by a connection of an inclined surface and a straight surface on the push button.

6. A lancing device as claimed in claim 2, wherein:
in the rotation route of the safety buckle in relation to the housing, a locating mechanism is set between the safety buckle and the housing, the locating mechanism comprises a concave point in one of the safety buckle and the housing and a convex point in the other, and the locating mechanism makes the safety buckle have two locating positions in the rotation route in relation to the housing, the two locating positions including (i) a first position corresponding to the first orientation and (ii) a second position corresponding to the second orientation, the convex point engaging with the concave point in one of the two locating positions, thereby restricting any further rotation of the safety buckle.

7. A lancing device as claimed in claim 6, wherein the convex point is blocked by a wall of the housing in the other of the two locating positions.

8. A lancing device having safety buckle turn lock and anti-backward push button, comprising;
a housing,
a trigger comprising a push button slideably located on the housing, and
a safety mechanism set between the push button and the housing to prevent unintentional triggering of a blood collection mechanism, the blood collection mechanism including a rotatable cam that rotates on an axis that is fixed relative to the housing, wherein:
a contact surface of the rotatable cam is at an initial position, and directly contacts the push button, prior to the push button being pushed;
the rotatable cam is rotated in a first direction as the contact surface is pushed by the push button;
the rotatable cam rotates in a second direction, opposite to the first direction, when the contact surface disengages from the push button;
a final position of the contact surface is a position rotated in the second direction relative to the initial position;
the safety mechanism includes a safety buckle that is turnably connected to the housing and has two orientations in a rotation route of the safety buckle in relation to the housing, the two orientations including (i) a first orientation between the push button and the housing to force the push button to be in a locking state before triggering and (ii) a second orientation, in a position separated from the first orientation, to make the push button be in an unlocking state;
between the push button and the cam on the blood collection mechanism, a locking mechanism is set to lock the push button after triggering, and the locking mechanism comprises a first locking part on the push button and a second locking part on the rotatable cam, and the first locking part and the second locking part meet during sliding of the push button and when the push button slides in a triggering direction, the first locking part and the second locking part meet to form a sliding engagement, but when the push button slides in a returning direction, the first locking part and the second locking part meet to form a locking engagement;
when the contact surface of the rotatable cam is at the initial position, the second locking part is at an initial locking part position rotated in the first direction relative to initial position, and is out of contact with the push button;
when the contact surface is at the final position, the second locking part is at a position rotated in the second direction relative to the initial locking part position; and
at a rotational connection of the safety buckle and the housing, one of the safety buckle and the housing includes a rotation shaft, and the other one includes a rotation shaft hole, so that the rotation shaft and the rotation shaft hole work together to realize the rotational connection.

9. A lancing device as claimed in claim 8, wherein a blade of the blood collection mechanism blade is mounted on an arm, the arm being rotatable relative to the housing, and the cam pushes the arm outward and also rotates the blade after the triggering.

10. A lancing device as claimed in claim 8, wherein:
in the rotation route of the safety buckle in relation to the housing, a locating mechanism is set between the safety buckle and the housing, the locating mechanism comprises a concave point in one of the safety buckle and the housing and a convex point in the other, and the locating mechanism makes the safety buckle have two locating positions in the rotation route in relation to the housing, the two locating positions including (i) a first position corresponding to the first orientation and (ii) a second position corresponding to the second orientation, the convex point engaging with the concave point in one of the two locating positions, thereby restricting any further rotation of the safety buckle.

11. A lancing device as claimed in claim 10, wherein the convex point is blocked by a wall of the housing in the other of the two locating positions.

12. A lancing device as claimed in claim 8, wherein:
in the rotation route of the safety buckle in relation to the housing, a locating mechanism is set between the safety buckle and the housing, the locating mechanism comprises a concave point in one of the safety buckle and the housing and a convex point in the other, and the locating mechanism makes the safety buckle have two locating positions in the rotation route in relation to the housing, the two locating positions including (i) a first position corresponding to the first orientation and (ii) a second position corresponding to the second orientation, the convex point engaging with the concave point in one of the two locating positions, thereby restricting any further rotation of the safety buckle.

13. A lancing device having safety buckle turn lock and anti-backward push button, comprising:
a housing,
a trigger comprising a push button slideably located on the housing,
a safety mechanism set between the push button and the housing to prevent unintentional triggering of a blood collection mechanism,
a rotatable cam that rotates on a first axis that is fixed relative to the housing, and
an arm on which a blade of the blood collection mechanism is mounted, the arm being rotatable on a second axis that is fixed relative to the housing, and the blade being rotatable about a third axis that is fixed relative to the arm, wherein:
the cam initially rotates counterclockwise about the first axis while being pushed by the push button, and after disengaging from the push button, rotates in a clockwise direction about the first axis;
while rotating in the clockwise direction, the cam (i) causes the arm to rotate in a counterclockwise direction about the second axis and (ii) causes the blade to rotate in a counterclockwise direction about the third axis; a cutting operation of the blade being caused by a combination of the rotation of the arm and the rotation of the blade;

the safety mechanism includes a safety buckle that is turnably connected to the housing and has two orientations in a rotation route of the safety buckle in relation to the housing, the two orientations including (i) a first orientation between the push button and the housing to force the push button to be in a locking state before triggering and (ii) a second orientation, in a position separated from the first orientation, to make the push button be in an unlocking state;

between the push button and the housing, or between the push button and the safety buckle, a locking mechanism is set to lock the push button after triggering, and the locking mechanism comprises a first locking part on the push button and a second locking part on the housing or the safety buckle, the first locking part and the second locking part meet during sliding of the push button and when the push button slides in a triggering direction, the first locking part and the second locking part meet to form a sliding engagement, but when the push button slides in a returning direction, the first locking part and the second locking part meet to form a locking engagement; and at a rotational connection of the safety buckle and the housing, one of the safety buckle and the housing includes a rotation shaft, and the other one includes a rotation shaft hole, so that the rotation shaft and the rotation shaft hole work together to realize the rotational connection.

14. A lancing device as claimed in claim 13, wherein: the first locking part is a slot on the push button and the second locking part is a wedge protruding rib on the housing, the wedge being in the slot after the triggering.

15. A lancing device as claimed in claim 13, wherein: the first locking part is a flexible hook on the push button and the second locking part is a convex on the housing.

16. A lancing device as claimed in claim 13, wherein: the first locking part is a flexible arm on the push button and the second locking part is a stopper on the housing.

17. A lancing device as claimed in claim 13, wherein: the second locking part includes a portion of the rotation shaft on the safety buckle that protrudes from the rotation shaft hole on the housing and the first locking part includes a flange formed by a connection of an inclined surface and a straight surface on the push button.

* * * * *